United States Patent
Dohse et al.

(10) Patent No.: US 9,511,980 B2
(45) Date of Patent: Dec. 6, 2016

(54) MEANS FOR FASTENING OR FOR CLAMPING GOODS, AND INFORMATION MEDIUM

(75) Inventors: Lars Dohse, Aachen (DE); Werner Glasen, Hofstadt (DE)

(73) Assignee: Spanset Inter AG, Oetwil am See (CH)

( * ) Notice: Subject to any disclaimer, the term of this patent is extended or adjusted under 35 U.S.C. 154(b) by 45 days.

(21) Appl. No.: 10/551,871

(22) PCT Filed: Jan. 7, 2005

(86) PCT No.: PCT/EP2005/000104
§ 371 (c)(1),
(2), (4) Date: Nov. 16, 2006

(87) PCT Pub. No.: WO2005/066061
PCT Pub. Date: Jul. 21, 2005

(65) Prior Publication Data
US 2007/0068123 A1    Mar. 29, 2007

(30) Foreign Application Priority Data

Jan. 8, 2004 (DE) .................. 10 2004 001 265

(51) Int. Cl.
| | | |
|---|---|---|
| B42D 15/00 | (2006.01) | |
| B66C 1/12 | (2006.01) | |
| B60P 7/08 | (2006.01) | |
| B66C 1/18 | (2006.01) | |
| A61B 19/00 | (2006.01) | |

(Continued)

(52) U.S. Cl.
CPC ............... *B66C 1/12* (2013.01); *B60P 7/0823* (2013.01); *B66C 1/18* (2013.01); *G09F 3/00* (2013.01); *A44C 5/0015* (2013.01); *A61B 19/44* (2013.01); *B42D 15/00* (2013.01); *B42P 2241/22* (2013.01); *G09F 3/005* (2013.01)

(58) Field of Classification Search
CPC ....... G09F 3/005; B42D 15/00; A44C 5/0015; A61B 19/44; B42P 241/22
USPC .................. 40/642.02, 633, 304, 665, 607.14
See application file for complete search history.

(56) References Cited

U.S. PATENT DOCUMENTS

| | | | | |
|---|---|---|---|---|
| 4,773,175 A | * | 9/1988 | Larsen | ............... 40/308 |
| 5,581,924 A | * | 12/1996 | Peterson | ............. 40/633 |
| 6,105,295 A | * | 8/2000 | Brinkman et al. | ......... 40/661.03 |

(Continued)

FOREIGN PATENT DOCUMENTS

| | | |
|---|---|---|
| DE | 81 02 337 U1 | 7/1981 |
| DE | 87 08 432 U1 | 8/1987 |
| DE | 94 14 241 U1 | 2/1995 |

OTHER PUBLICATIONS

International Search Report for PCT/EP2005/000104 (in English and German).

*Primary Examiner* — Syed A Islam
(74) *Attorney, Agent, or Firm* — The Webb Law Firm

(57) ABSTRACT

For the fastening, securing or clamping of goods, such as a load strap, support strap, tie member, rope, safety harness or the like, with an information medium (2) attached thereto, wherein it is ensured, even under hard operating conditions, that the prescribed marking is maintained for a long time, this is achieved in that the information medium (2) includes at least one identification medium (3*a*, 3*b*), an insert (4) having high tear strength, to which the identification medium (3*a*, 3*b*) is attached, and a protective casing (5), which surrounds the identification medium (3*a*, 3*b*) and the insert (4).

33 Claims, 2 Drawing Sheets

(51) Int. Cl.
  *G09F 3/00* (2006.01)
  *A44C 5/00* (2006.01)

(56) References Cited

U.S. PATENT DOCUMENTS

| | | | |
|---|---|---|---|
| 6,632,042 B1 * | 10/2003 | Liener Chin et al. | 402/79 |
| 6,644,694 B2 * | 11/2003 | Seawright | 283/34 |
| 2004/0250459 A1 * | 12/2004 | Brinkman et al. | 40/642.02 |

* cited by examiner

MEANS FOR FASTENING OR FOR CLAMPING GOODS, AND INFORMATION MEDIUM

BACKGROUND OF THE INVENTION

The invention relates to a means for fastening, securing or clamping goods or for securing a person, such as a load strap, support strap, tie member, rope and safety harnesses or the like, with an information medium attached thereto. Products of this type are used, for example, for lifting, conveying and fastening items of cargo and for harnessing persons.

The invention also relates to an information medium for attachment to a fastening or clamping means of the aforementioned type, which medium is used to impart to the user important product-specific information regarding the fastening or clamping means to be used. Examples of such information include the product name, the maximum carrying capacity or load, brief instructions, etc.

The information media that have been used in the past generally consist either of a direct imprint of the information on the corresponding fastening or clamping means or else of a printed fabric strip, which is in turn connected to the corresponding fastening or clamping means or PSE product ("PSE"=person securing equipment). This connection may be produced, for example, by sewing-on.

However, the drawback of the described prior art is that, over the course of time, as a result of the high loads, especially owing to friction or stretching, which act on the fastening or clamping means and PSE products, the information medium may become damaged or even become torn off. Moreover, fluttering in the air stream of an information medium that is only attached on one side results in fatigue breaks at the attachment point. The printed regions may also gradually become worn, as a result of which the information becomes illegible or at least difficult to recognise. This has a negative effect on user-friendliness and product safety.

Moreover, very high-quality, expensive products of the type in question may often generally no longer be used as soon as the relevant information can no longer be optimally determined. This is particularly serious if the information medium becomes detached during use from the respective fastening or clamping means or from the PSE product as a result of an external load. The loss of the information medium generally entails immediate loss of the authorisation.

German utility model specification DE 81 02 337 U1 discloses a lifting strap, which comprises a first label, which is sewn into a clip or strap seam and contains the information pertaining to the lifting strap. In order to prevent premature loss of the information required for the authorisation of the lifting strap, a second label, which protrudes only slightly beyond the joint of the strip, which is turned up in the region of the seam, is also sewn into the relevant seam. This second label, which is substantially shorter, is provided with data that is absolutely essential for the authorisation and must be available for as long as the strip is in use. As a result of the fact that the second label protrudes only very slightly beyond the seam region, it shall be protected from damage by the bead formed by the strip, which bead is turned up in the seam region. However, the problem with this type of protection is that the protective effect of the bead is only provided over a very short length and is also dependent on the thickness of the bead. In so far as the protective effect is provided at all, only a small area, which in practice is not sufficient to be able to ensure the prescribed marking of a lifting strap in a legible form under practice conditions, is therefore available on the label. Moreover, in the case of this prior art, it may also occur that the first and second labels become worn and are detached prematurely from the lifting strap owing to the movements, which in practice occur continuously, in the seam region.

SUMMARY OF THE INVENTION

Starting from the above-described prior art, the object of the invention was to provide a means of the type mentioned at the outset and a correspondingly suitable information medium with which it is ensured, even under hard operating conditions, that the prescribed marking is maintained over a long period of time.

With respect to the means for fastening, securing or clamping goods, such as a load strap, support strap, tie member, rope, safety harness or the like, with an information medium attached thereto, this object is achieved, according to the invention, in that the information medium consists of at least one identification medium, an insert having high tear strength and a protective casing, which surrounds at least the identification medium.

With respect to the information medium for marking a means for fastening, securing or clamping goods or for securing a person, such as a load strap, support strap, tie member, rope, safety harness or the like, the above-mentioned object is achieved, according to the invention, in that it consists of at least one respective identification medium, an insert having high tear strength and a protective casing, which surrounds at least the identification medium, and is joined as a unit independently of the means.

The information medium according to the invention is multilayered. An individual function is associated with each of the layers of the information medium, so the layers may each be made of an optimally suitable material for their function. Thus, the identification medium provided as an information carrier may be a label made of a material that may be optimally printed and still ensures good readability even after extended use. Similarly, the identification medium may be selected such that it is optimally suitable as a carrier of information that may be machine-read optically, electronically or in another form.

Each identification medium may be selected without taking into account a specific strength required for permanent attachment, as it is protected from premature destruction by the insert having high tear strength. Materials that have only low tear strength may thus be used for the identification medium. In this eventuality, too, the insert, which in this case has a higher tear strength than the identification medium, ensures that the identification medium remains securely attached over the entire duration of the use of the correspondingly marked lifting means, securing means, clamping means or PSE product.

In the event of an externally acting load, the identification medium rests on and is supported by the insert having high tear strength. The insert having high tear strength thus absorbs all of the tensile and bending forces acting on the information medium and prevents the various layers of the information medium from becoming damaged by these forces.

Finally, the protection of the identification medium against abrasion or similar external influences is safeguarded by the casing, which is placed around the identification medium and the insert. This casing protects the identification medium and the insert, in particular, from atmospheric influences and direct mechanical contact with foreign elements. As it, too, is protected by the insert having high tear strength from destruction in the event of tensile or bending forces acting on it, the protective casing may be made of a soft, weatherproof and shock-absorbing material, without itself having a high tear strength.

The configuration according to the invention of an information medium thus ensures that the product-specific information is maintained and easily readable at all times, even after a long time and in the event of frequent use. The life expectancy of an information medium according to the invention is therefore significantly increased. Accordingly, the invention ensures that a fastening, clamping and securing means configured according to the invention remains marked in the prescribed manner until it reaches its destination, and the risk of a premature loss of the authorisation, as a result of its marking becoming unusable, is reduced to a minimum.

The protective casing may be configured as a tube, film or protective coating and be made, for example, of a plastics material, especially of polyethylene (PE) or of polyvinyl chloride (PVC). The casing is preferably transparent in order to allow the identification medium to be read easily. It should also be UV-resistant, so as to ensure that it continues to operate optimally even after extended use.

In order to ensure sufficient flexibility, in cases in which the casing is made of PE or PVC material, the thickness of the casing should be no more than 1 millimeter. Practical tests have revealed a thickness of 0.3 mm+/−0.1 mm to be the optimal material thickness of the casing.

According to a preferred embodiment, the insert having high tear strength is made of a technical textile, especially a fabric, and is, in particular, strip-shaped, so as to allow even a relatively long identification medium to be supported without difficulty, with a simplified fastening. The separate insert increases the rigidity, and hence the strength, of the information medium, and this counteracts, in particular, fluttering of the information medium in the air stream and significantly reduces the risk of a fatigue break of the identification medium.

In the case of the use of an, especially strip-shaped, insert having high tear strength (but also such an insert of any other shape), at least one identification medium may be provided on each side. Thus, for example, a label including the product name and the product information required by the relevant standards, such as the maximum load, may be attached to the leading side of the insert and a label including brief directions for using the product may be attached to the trailing side. It is also conceivable to arrange a machine-readable identification medium on one side of the insert, while as an identification medium a label, on which the necessary information is specified in plain text, is provided on the other side of the insert.

The label may be sewn, glued and/or riveted to the insert. It is also conceivable to position portions of the identification medium on both sides of the insert in that, in the case of a strip-shaped identification medium, a strip portion, which is provided with the necessary information, of the identification medium is placed around the insert having high tear strength, so one strip portion extends on the leading side, in the direction of the insert, and the other label strip portion extends on the other side of the insert having high tear strength.

Especially if the fastening means, clamping means or PSE product is made, at least in certain sections, of a textile material, for example is woven, the information medium may be attached to it in a simple manner by sewing-on. However, sewing-on is also possible if the fastening or clamping means is made of a different material. It is, of course, also conceivable that the information medium is glued and/or riveted to the fastening or clamping means. In this case, too, only one end of the information medium may be connected to the fastening or clamping means. Ultimately, all that matters is that this connection is able to withstand high loads.

If a machine-readable identification medium is used, simplified material management may, for example, be facilitated in that the location of the correspondingly marked support, securing or clamping means is detected using suitable detectors in a storage means. Moreover, the identification medium also allows the material output and return to be organised in a simple manner. Furthermore, the legally prescribed data for an inspection may be read directly into a data processing system and compared with the scheduled data contained therein.

A machine-readable identification medium may be produced in a cost-effective manner in that it is a transponder. However, it is also conceivable to attach an optically scannable bar code or other machine-readable information to the identification medium.

Depending on the type of the respective identification medium used, it may be expedient to attach this identification medium directly to the insert. This ensures that the insert, with its high tear strength, continues to operate even in the case of identification media that are sensitive to tensile or compression loads. For this purpose, the identification medium may be rigidly connected, especially sewn, riveted and/or glued, to the insert.

Especially if the identification medium is carried by the insert having higher tear strength or is formed as a label, it may be sufficient for only a portion of the information medium to be connected directly to the fastening or clamping means. This is the case, for example, if an elongate label, which is connected to the respective lifting, clamping or securing means only on a narrow side, is used as the identification medium.

The identification medium may be covered with a protective layer in order to prevent damage caused by external influences. In this case, the protective layer may be made of a flexible plastics material, for example a silicone or polyurethane, which is able to respond to the movements of the information medium.

BRIEF DESCRIPTION OF THE DRAWINGS

The invention will be described below in greater detail with reference to a drawing, which illustrate an embodiment and in which.

DETAILED DESCRIPTION OF THE INVENTION

Figure 1:
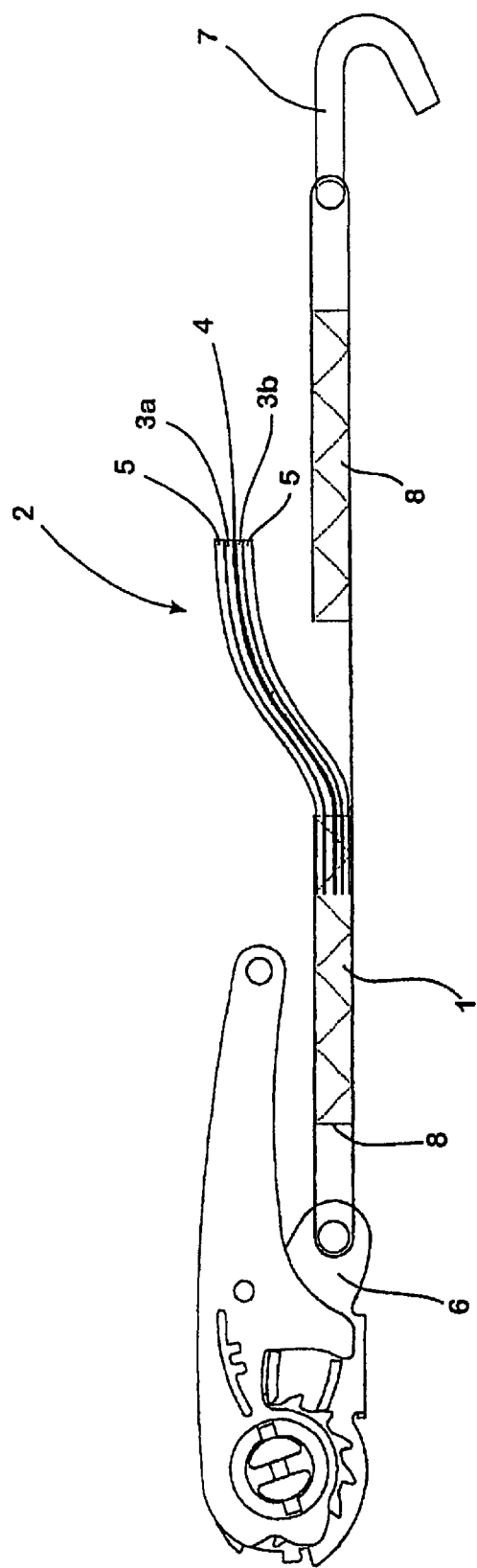
FIG. 1 is a schematic lateral view of an end portion of a load strap.

The load strap 1 illustrated in FIG. 1, which acts as a fastening or clamping means, forms, in the region of its ends for the attachment of a ratchet 6 or a hook 7, a loop in which its one end has been folded, thus forming the loop, and placed on the end portion of the load strap 1. In order to prevent this loop from becoming accidentally detached, even in the event of high loads, the load strap is sewn in this region. The corresponding seam 8 is illustrated in FIG. I by a broken line.

An information medium 2 is also attached to the load strap 1 by means of this same seam 8. The information medium 2 comprises a strip-shaped, woven insert 4, to which an identification medium 3a, which is configured as a label, is attached. The product name and information required by the relevant standards, such as the maximum load, are printed on the identification medium 3a.

A further identification medium 3b, which is configured in the manner of a label and on which brief directions for using the load strap are printed, is attached to the trailing side of the insert 4. The insert 4, with the two identification media 3a and 3b attached thereto, is surrounded by a protective casing 5, which is made of a durable and UV-resistant plastics material and is 0.3 mm thick. As the protective casing 5 is transparent, the identification media 3a and 3b located beneath it may easily be read.

The identification media 3a, 3b may be formed by portions of a strip, which is oriented in the longitudinal direction of the insert 4 having high tear strength and is placed around the end of said insert that is associated with the fastening means 1, where it is sewn, together with the insert 4, to the fastening means 1. The portion, which is thus located movably on the upper side of the insert 4, of the strip then forms the identification medium 3a, while the strip portion extending along the trailing side of the insert 4 forms the identification medium 3b.

The information medium 2 is connected to the fastening or clamping means 1, via the seam 8, merely at one end. The information medium 2 may thus be folded onto the load strap on both sides, so the information medium 2 is always highly visible even when lifting, conveying, securing or fastening items of cargo having different shapes.

The fastening or clamping means 1 described above by way of example and the corresponding information medium 2 ensure, as a result of the strong and durable multilayered structure of the information medium 2, that the product-specific information may easily be read even after a long time. Moreover, the risk of a fatigue break caused by fluttering of the information medium 2 in the air stream is also significantly reduced as a result of the multilayered, solid structure. Tearing-out, in particular, is prevented by the underlaying of the strap. In the past, the material of the identification medium was the weak point, as, on the one hand, it had to be easily imprintable and, on the other hand, it had to be able to withstand high mechanical loads. The region of the sewing-in zone, on which, in the prior art, the identification medium was sewn to the respective strap (conveying, securing or lifting means), was, as a result of the perforation entailed by sewing, especially prone to tearing. The invention obviates this problem, as the insert having high tear strength supports the identification medium, so the mechanical loads that occur in practical use no longer affect the material of the identification medium as markedly as in the prior art.

Figure 2:
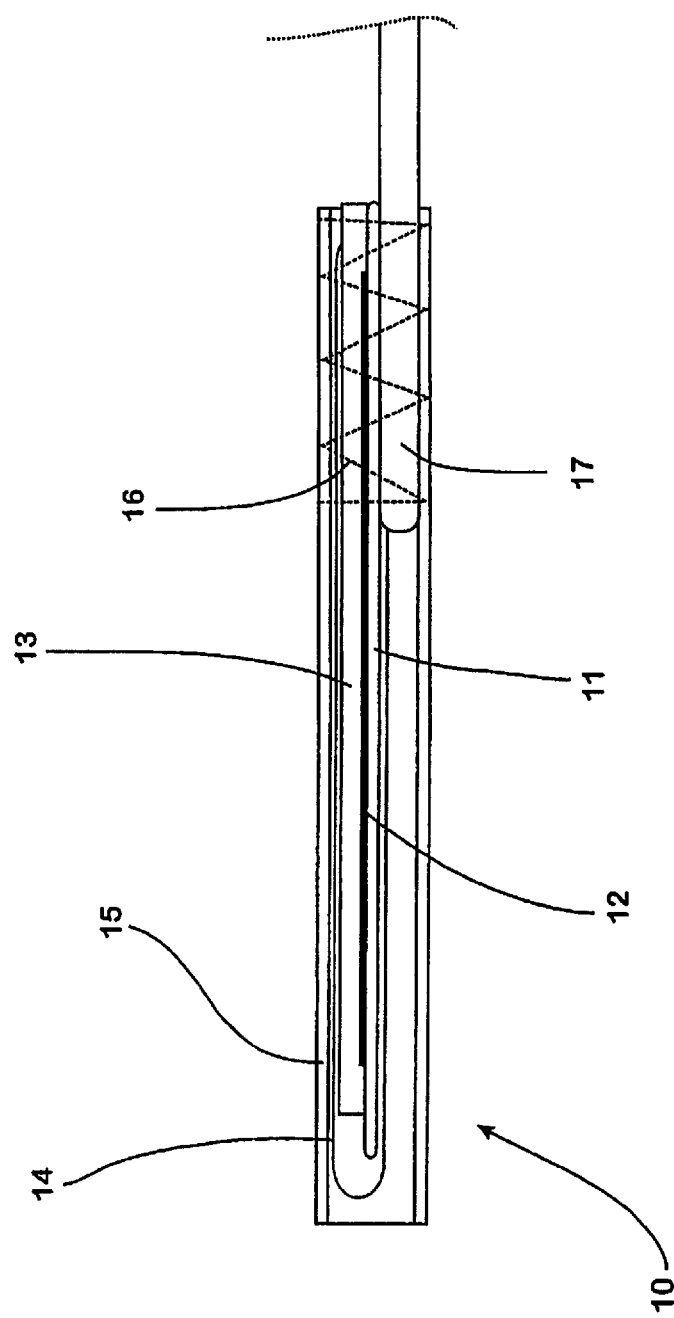
FIG. 2 is a schematic lateral view of an information medium.

The information medium 10 illustrated in FIG. 2 comprises a strip-shaped layer 11 that has high tear strength and is made of a technical fabric, such as is used, for example, for the manufacture of straps, etc. The insert 11 having high tear strength contains on its upper side an identification medium 12, which is glued, for example, to the surface of the insert 11. The identification medium 12 is, for example, a commercially available transponder, which is encoded in a suitable manner so as to allow an unambiguous identification of the strap, carriers, etc. equipped with the information medium 10. The identification medium 12 allows inventories, sites of installation and action times and similar factors relevant to the prescribed use of goods marked according to the invention, which factors may be crucial for the safe use of these goods, to be collected in a simple manner.

In order to prevent damage caused by external loads, the identification medium 12 is covered with a flexible plastics material layer 13, which is formed, for example, by a polyurethane applied to the layer 11 having high tear strength.

A likewise label-like identification medium 14, which covers the upper and lower sides of the insert, is placed around the insert 11 having high tear strength and comprising the identification medium 12 and the plastics material layer 13 in the longitudinal direction of the insert 11. The necessary product information is printed out on the respective outer surface of the identification medium 14. The material of the identification medium 14 is selected such that it may easily be imprinted and placed around the insert 11.

A transparent tube made of PVC, which covers the identification medium 14 and, with it, the insert 11 having high tear strength and comprising the identification medium 12 and the plastics material layer 13 on all sides, is placed over the identification medium 14 as a protective casing 15. The insert 11 having high tear strength and comprising the identification medium 12 and the plastics material layer 13, the identification medium 14, which surrounds the insert 11, viewed in the longitudinal direction, and the protective casing 15 thus form a stack of material layers, which together form the information medium 10.

At its one end, viewed in the longitudinal direction, this information medium 10 is sewn to the end of a support strap 17 by means of a seam 16. In practical use, the protective casing 15 protects the identification medium 14 and the transponder 12 from external influences. At the same time, the layer having high tear strength ensures that the information medium 10 is able to withstand even high mechanical loads, thus effectively preventing tearing from the end of the support strap 17.

REFERENCE NUMERALS

1 Fastening or clamping means
2 Information medium
3a Identification medium
3b Identification medium
4 Insert
5 Protective casing
6 Ratchet
7 Hook
8 Seam
10 Information medium
11 Strip-shaped insert having high tear strength
12 Identification medium
13 Plastics material layer
14 Identification medium
15 Protective casing
16 Seam
17 Support strap

The invention claimed is:

1. Means for fastening, securing or clamping goods or for securing a person, said means comprising:
 (a) a strap having a first end, wherein the strap has an upper surface and a lower surface; and
 (b) an information medium permanently and rigidly connected to the first end of the strap,
 wherein only a portion of the information medium is connected directly to the strap;

wherein the information medium overlaps with the first end of the strap;

wherein the information medium consists of at least one identification medium, a strip shaped insert, different from the at least one identification medium, having high tear strength, and a protective casing, which surrounds the at least one identification medium and the insert having high tear strength;

wherein the at least one identification medium, the insert, and the protective casing are joined to form a durable unit with a multilayered structure; and wherein the strip shaped insert overlaps with the first end of the strap, whereby a portion of the strip shaped insert overlapping the first end of the strap is disposed within a vector normal to the upper or lower surface of the first end of the strap.

2. Means according to claim 1, wherein the strap for fastening, securing or clamping goods or person is sewn to the information medium.

3. Means according to claim 1, wherein the strap for fastening, securing or clamping goods or person is glued and/or riveted to the information medium.

4. Means according to claim 1, wherein the identification medium is readable.

5. Means according to claim 4, wherein the identification medium is machine-readable.

6. Means according to claim 1, wherein the insert has a higher tear strength than the identification medium.

7. Means according to claim 1, wherein the insert consists of a technical textile, especially a fabric.

8. Means according to claim 1, wherein the insert is strip-shaped.

9. Means according to claim 1, wherein the insert acts on both sides as a carrier of identification media.

10. Means according to claim 1, wherein the identification medium is rigidly connected, especially sewn and/or riveted and/or glued, to the insert.

11. Means according to claim 1, wherein the protective casing is a tube or a film.

12. Means according to claim 1, wherein the protective casing is made of plastics material, especially of polyethylene (PE) or of polyvinyl chloride (PVC).

13. Means according to claim 1, wherein the protective casing is transparent.

14. Means according to claim 1, wherein the identification medium is a label provided with information.

15. Means according to claim 1, wherein the identification medium is a transponder.

16. Means according to claim 1, wherein the identification medium is carried by the insert.

17. Means according to claim 1, wherein the at least one identification medium is covered by a protective layer.

18. Means according to claim 17, wherein the protective layer is a flexible plastics material.

19. Means according to claim 18, wherein the flexible plastics material is a silicone or polyurethane.

20. Means according to claim 1, wherein the protective casing is made of a UV-resistant material.

21. Means according to claim 1, wherein the strap for fastening, securing or clamping goods or person is a load strap, support strap, tie member, rope, or safety harness.

22. Means according to claim 1, wherein the strap for fastening, securing or clamping goods or a person comprises multiple sections connected by a web.

23. Means according to claim 1, wherein the at least one identification medium, the insert, and the protective casing are permanently joined to form the durable unit.

24. A device for fastening, securing or clamping goods or for securing a person, the device comprising:

a strap having a first end, wherein the strap has an upper surface and a lower surface;

an information medium connected to the first end of the strap, wherein only a portion of the information medium is connected directly to the strap, wherein the information medium comprises:

a strip shaped insert overlapping with the first end of the strap, whereby a portion of the strip shaped insert overlapping the first end of the strap is disposed within a vector normal to the upper or lower surface of the first send of the strap;

an identification medium on the strip shaped insert, wherein the strip shaped insert has a higher tear strength than the identification medium; and a protective casing covering at least the entire identification medium.

25. The device according to claim 24, wherein the first end is folded, thus forming an attachment loop.

26. The device according to claim 25, wherein the information medium is connected to the first end of the strap outside of the attachment loop.

27. The device according to claim 25, further comprising a ratchet or hook attached to the first end of the strap via the attachment loop.

28. The device according to claim 25, wherein the strap is sewn together to prevent the attachment loop from becoming accidentally detached.

29. The device according to claim 28, wherein the first end of the strap and the information medium are sewn together by the same seam that prevents the attachment loop from becoming accidentally detached.

30. The device according to claim 24, wherein the information medium is a transponder.

31. The device according to claim 30, wherein the transponder is covered with a flexible plastics material layer.

32. The device according to claim 31, further comprising a label which covers upper and lower sides of the insert, the transponder, and the flexible plastics material layer.

33. The device according to claim 31, wherein the protective casing covers the insert, the transponder, the flexible plastics material layer, and the label on all sides.

* * * * *